US00PP17751P3

(12) United States Plant Patent
Duvall

(10) Patent No.: US PP17,751 P3
(45) Date of Patent: May 22, 2007

(54) ***VIBURNUM* PLANT NAMED 'DUVONE'**

(50) Latin Name: *Viburnum×burkwoodii*
Varietal Denomination: Duvone

(76) Inventor: W. Andrew Duvall, 9950 Dixboro Rd., South Lyon, MI (US) 48178

( * ) Notice: Subject to any disclaimer, the term of this patent is extended or adjusted under 35 U.S.C. 154(b) by 114 days.

(21) Appl. No.: 11/074,819

(22) Filed: Mar. 8, 2005

(65) Prior Publication Data

US 2006/0206972 P1 Sep. 14, 2006

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent Bell
(74) *Attorney, Agent, or Firm*—James M. Deimen

(57) ABSTRACT

A new and distinct *viburnum* plant named 'Duvone' which is distinguished by the same characteristics which make it a valuable ornamental plant; specifically, abundant spicy fragrant flowers, glossy foliage, multi-hued autumn color developing and holding after most deciduous plants have defoliated, and slow growth and tidy habit suitable for smaller scale low maintenance landscapes.

6 Drawing Sheets

BACKGROUND OF THE INVENTION

The present invention relates to a new and distinct cultivar of burkwood *viburnum* botanically known as *Viburnum× burkwoodii,* hereinafter referred to by the cultivar name 'Duvone'. The invention is denominated a deciduous flowering shrub.

DISCOVERY OF THE INVENTION

The original plant, a spontaneous whole plant mutation of *Viburnum×burkwoodii* 'Sarcoxie,' was discovered by the applicant as an individual plant within a block of 'Sarcoxie' not patented, in September 1997. The plant was located in the west central area of Block SW-1 on the applicant's nursery in Parcel B-02-01-2-00-15 Northfield Township, Washtenaw County, South Lyon, Mich. 48178.

PROPAGATION

Asexual propagation of 'Duvone' has been accomplished at the applicant's propagation facility located one mile due east of the location of discovery, as detailed above.

The new plant has been reproduced by vegetative summer softwood cuttings from the original plant as well as from second and third generation plants. In all cases, subsequent generations have remained identical to the original plant in all distinguishing characteristics.

SUMMARY OF THE INVENTION

The following traits have been repeatedly observed and are the unique characteristics of 'Duvone.' In combination, these characteristics distinguish the new *Viburnum burkwoodii* as a new and distinct cultivar. Color references are made to The Royal Horticultural Society Colour Chart, except where general terms of ordinary dictionary significance are used. The following characteristics describe the ornamental value and distinguishing features of 'Duvone' as observed from an 8-year old plant 1.2 m in height, 1.3 m in width, growing in an outdoor garden in South Lyon, Mich.

While 'Duvone' more closely resembles 'Sarcoxie' than any other *viburnum* known to the inventor, it differs in three distinct aspects. (FIG. 1—'Duvone' is to the left of 'Sarcoxie'. Both plants were rooted at the same time and have been grown under identical conditions.) The habit of 'Duvone' is rounded and compact, whereas 'Sarcoxie' is taller and more upright. Flowers and foliage develop two to three days earlier on 'Duvone' than 'Sarcoxie.' Finally, 'Duvone' flowers have a very pleasant strong clove-like spicy fragrance, whereas 'Sarcoxie' has a somewhat unpleasant fragrance.

FLOWERS

Coral pink buds, 49D, become effective in late April and open to pure white flowers, 155D. Flowering is profuse and complements glossy, crinkled emerging leaves (FIG. 2 and FIG. 7). The flowers are in full bloom in early May and are effective for 10 to 14 days.

FOLIAGE

Changing foliage offers interest throughout the seasons. Young glossy, crinkled leaves mature to a lustrous green by mid-June. While autumn coloration and time of color development may vary somewhat with the season, fall color is both spectacular and definitive. The plant consistently produces a multi-hued display of red, 46B, purple, 79A, orange, 28A, and yellow, 10B (FIG. 3). The plant develops its autumn color late, retaining its excellent green summer foliage as a contrast to normal autumn colors (FIG. 4). It then develops its characteristic coloration that remains after most other deciduous plants have defoliated (FIG. 5), often extending the color season until snowfall. This delayed multi-hued autumn coloration is unique among *viburnum.* (Locally, only *Pyrus calleryana* 'Bradford' still shows effective coloration at this time.) Fall color appears in late October, peaks in early to mid-November and remains effective until late November and occasionally early December.

HABIT

'Duvone' has a very neat, tidy appearance through all seasons. Under nursery culture, it has a vigorous upright habit. In a landscape situation, the growth rate slows markedly and it develops a very dense compact rounded habit (FIG. 6). This change is due to the tendency of 95–100 percent of shoots to produce only three short internodes before terminating in a flower bud. This property not only restricts the size of the plant but also enhances flowering.

CULTURE

Propagation by summer softwood cuttings. Culture as per other fragrant *viburnums*. Transplants readily balled and burlapped or from container. Sun or partial shade. Soil tolerant. Vigorous growth fosters economic nursery production.

HARDINESS

Hardy to USDA Hardiness Zone 5.

USE

Anywhere all season color and interest is desired. Foundation planting, accents, mass plantings, focal points, flowering hedges. The slow growth rate and moderate size are appropriate for low maintenance residential scale landscapes.

PESTS

None serious. Aphids and mites have been observed. Foliage appears to be disease resistant. No deer damage, either browsing or rubs, has been observed.

DESCRIPTION OF THE PREFERRED EMBODIMENTS

Figure 1:
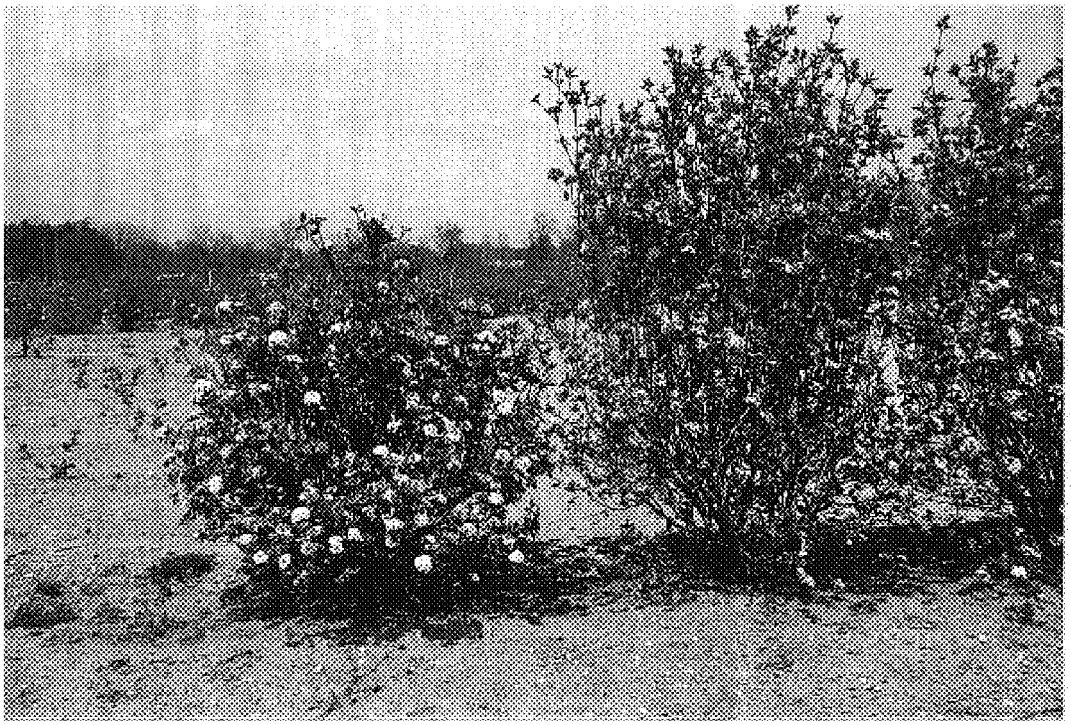
FIG. 1 is a colored photograph illustrating the differences between 'Duvone' on the left and *Viburnum×burkwoodii* 'Sarcoxie' on the right.
Figure 2:
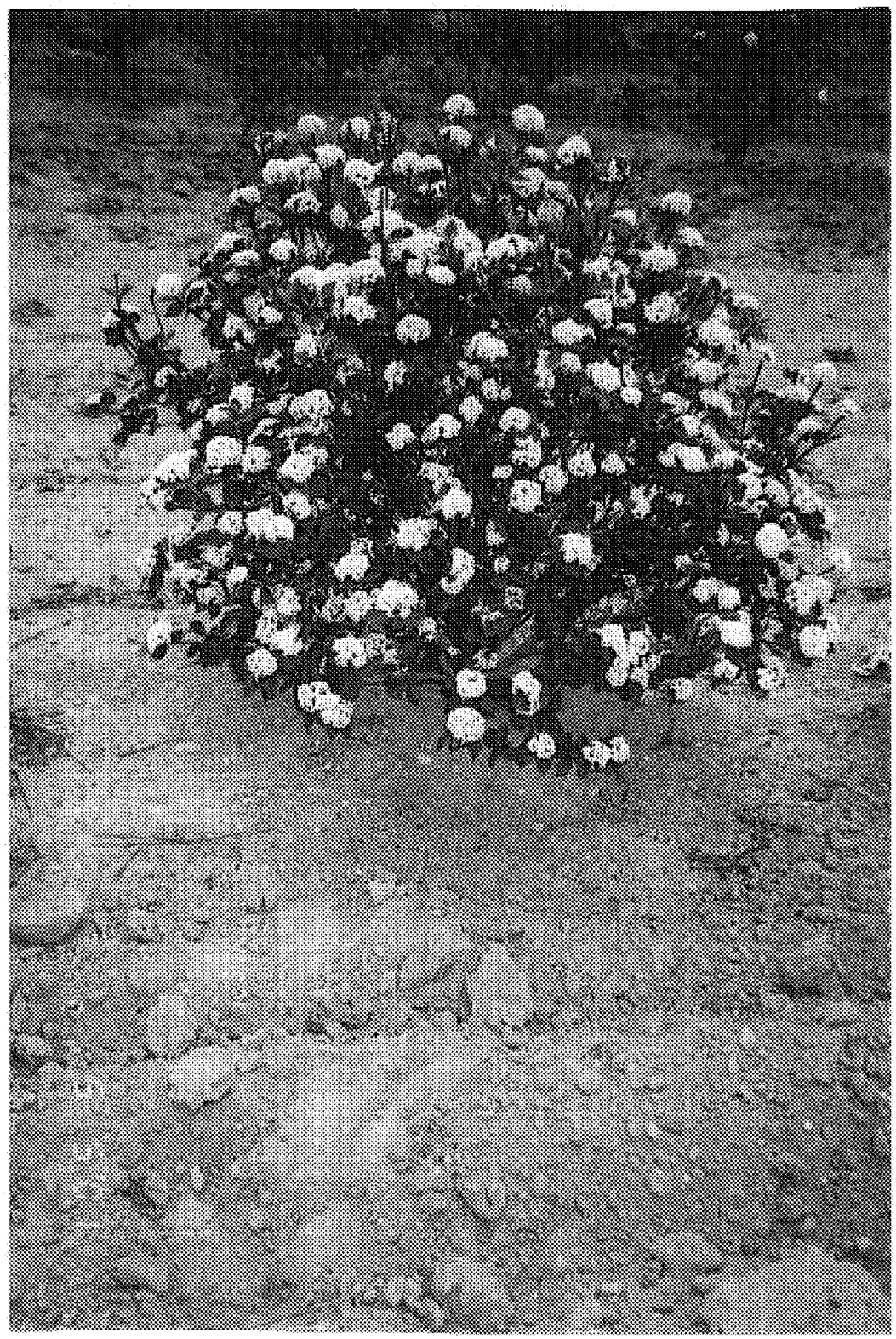
FIG. 2 is a colored photograph illustrating 'Duvone' in flower.
Figure 3:
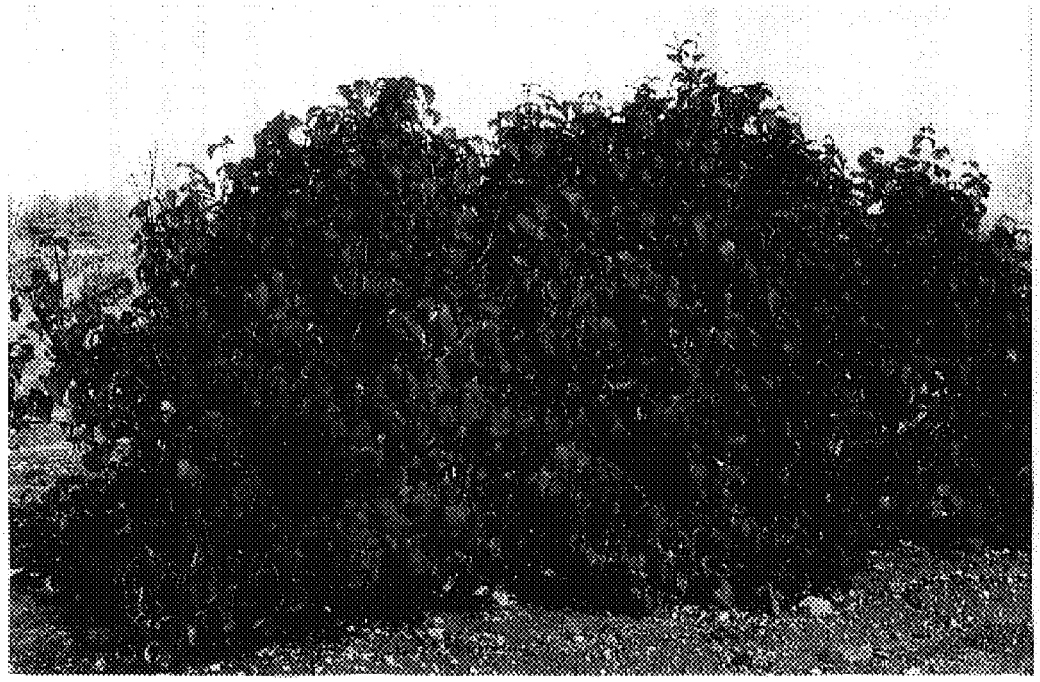
FIG. 3 is a colored photograph illustrating fall coloration.
Figure 4:
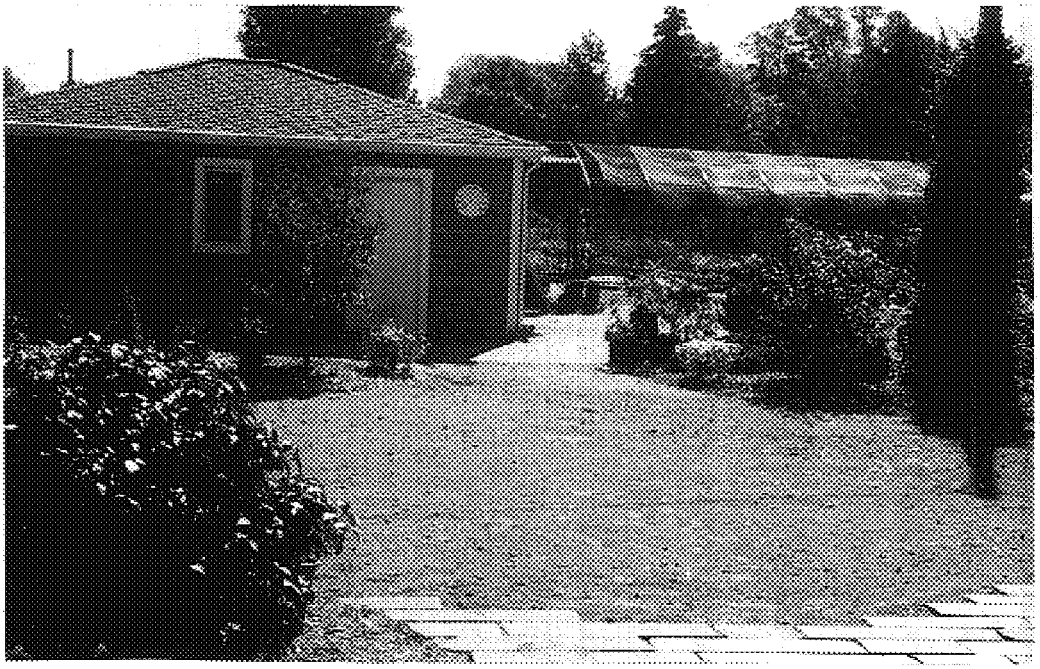
FIG. 4 is a colored photograph illustrating retention of summer foliage concurrent with "normal" deciduous fall color. 'Duvone' is in lower left foreground. Photograph taken Oct. 12, 2003.
Figure 5:
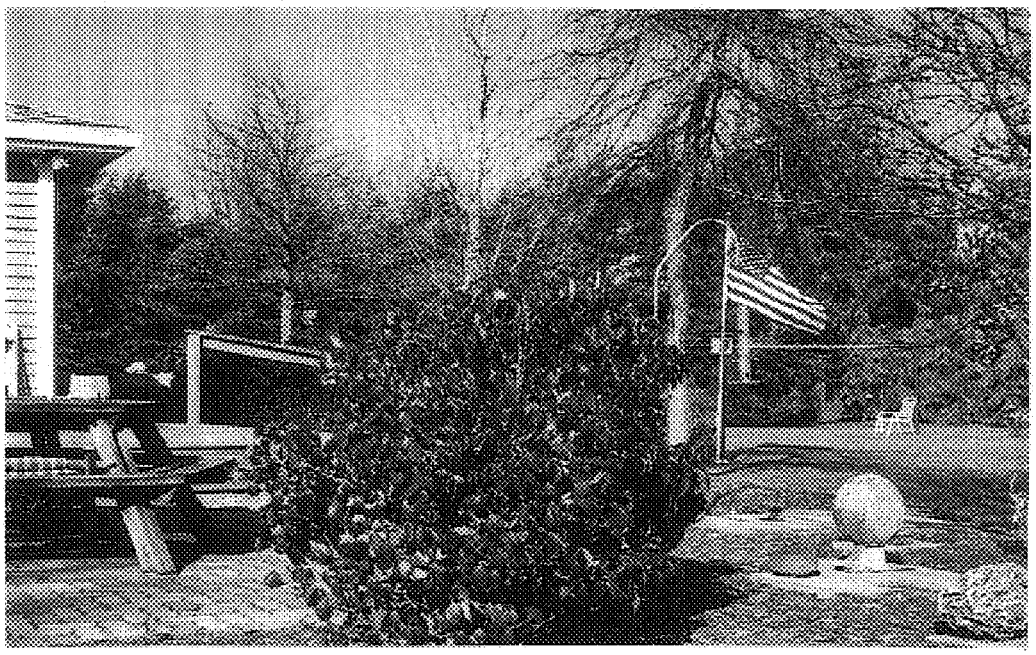
FIG. 5 is a colored photograph illustrating effective fall color of 'Duvone' remaining after other deciduous plants have defoliated. Photograph taken Nov. 14, 2003.
Figure 6:
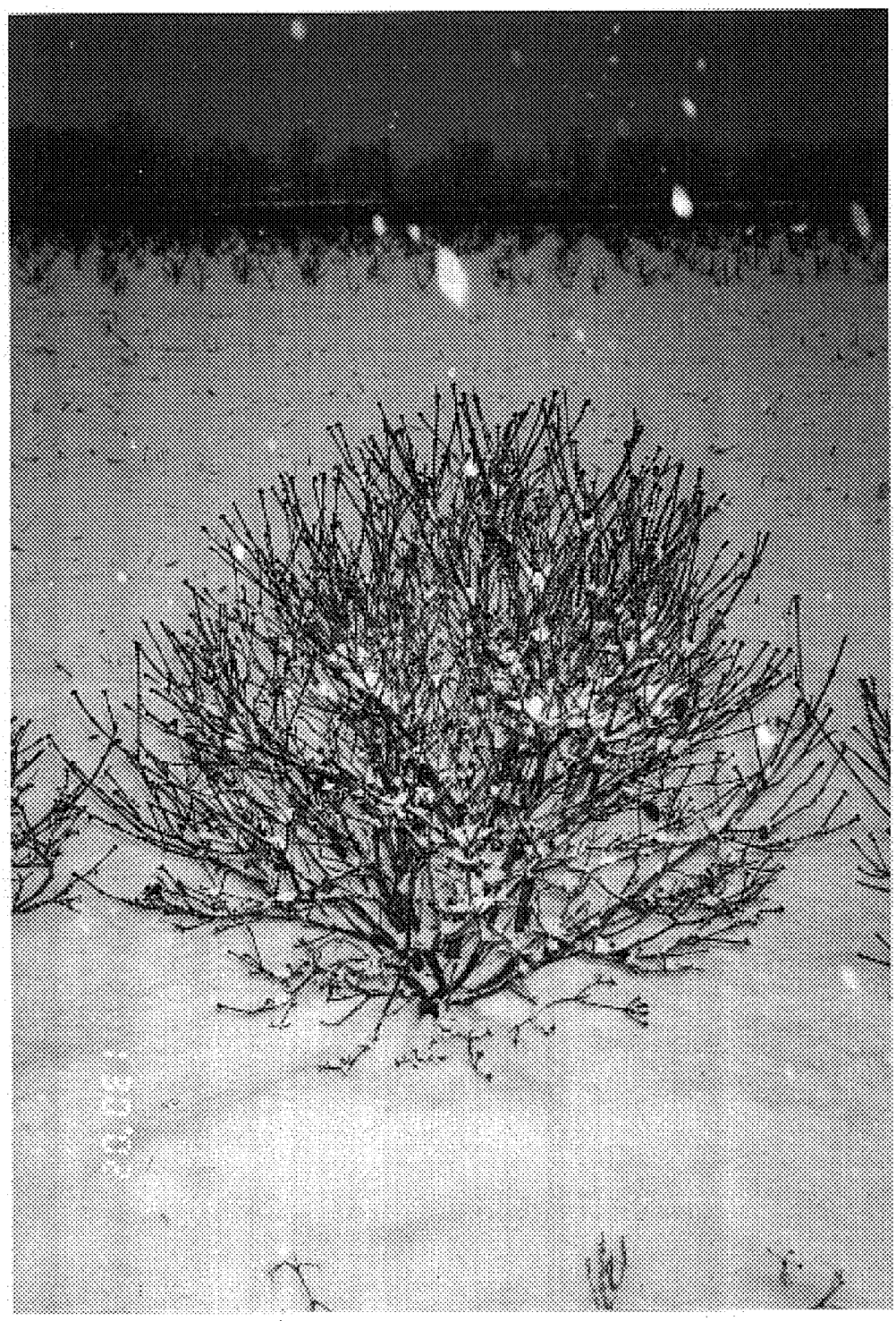
FIG. 6 is a winter photograph showing the habit and branching character.
Figure 7:
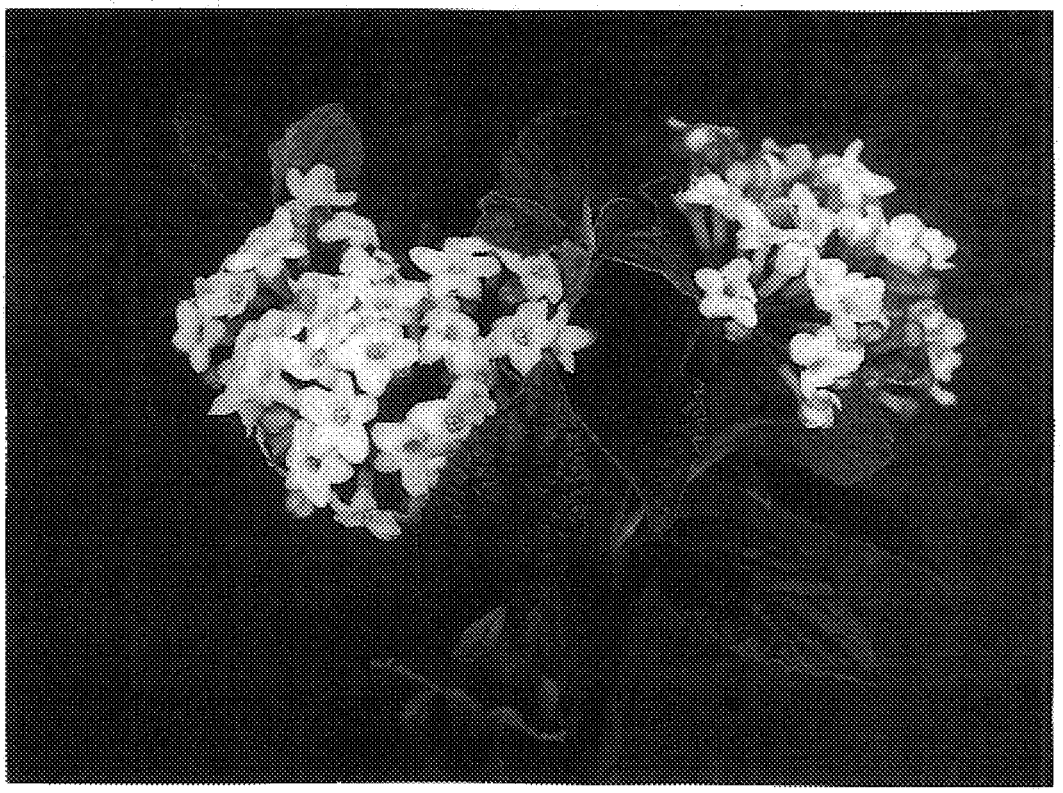
FIG. 7 is a close-up photograph showing the buds, flowers and adjacent foliage.

The following is a detailed description of my new and distinct variety of fragrant *Viburnum×burkwoodii* cultivar 'Duvone' discovered and grown outdoors at South Lyon, Mich. The plant as described is 1.2 m in height by 1.3 m in width at 8 years of age. Reference numbers are made to specific colors on the chart issued by The Royal Horticultural Society, London, England.

Botanical classification: *Viburnum×burkwoodii*'Duvone.'

Parentage: A spontaneous whole plant mutation of *Viburnum×burkwoodii* 'Sarcoxie,' not patented, discovered by the applicant at South Lyon, Mich.

Form/size: Compact rounded deciduous shrub. Original plant propagated as a cutting in 1992 is now 1.3 m wide by 1.2 m tall. This plant was transplanted in 1997, sheared in 1999, again transplanted in 2002.

Growth rate: Young plants under nursery conditions vigorous and upright, annual growth 30 to 45 cm per year; mature plants rounded and slow growing, annual growth 13 to 16 cm per year.

Hardiness: Hardy in USDA Hardiness Zone 5. Survived the winter of 1993–94 with 10 consecutive days of minus 20 degrees F. low temperatures and high temperature never reaching 0 degrees F. with no snow cover as a first year field transplant, then undiscovered.

Twigs and stems: Branches of current year 3–5 mm wide, stiff, ascending, branch angle 29 to 37 degrees, densely stellate, 176 B; primary branches 13–16 cm long, lateral branches 5–9 cm long; internodes mostly 2–10 cm long, except on rapidly growing shoots; older twigs, 199A, becoming glabrous, bark irregularly low ridged; vegetative winter buds naked, lanceolate, densely stellate, 4–14 mm long, 177A. Dormant flower bud plus or minus hemispherical, 8–10 mm wide, 5–7 mm high, 176B; pith white, 155D, continuous.

Leaves: Opposite, simple, typically 6 per lateral branch; petioles 4–10 (–15) mm long; 3.0–3.5 mm diameter at base, 2.0–2.5 mm diameter mid-petiole, 1.5–2.0 mm at blade junction, 47A; blades coriaceous, broadly elliptic to very broadly ovate, (3-) 5–9 cm long, (2-) 3–7 cm wide, the apex acute, the base broadly cuneate to rounded or even subcordate on the largest leaves, the margins shallowly and irregularly dentate with 2–4 teeth/cm, becoming plus or minus entire near apex; pinnately 3–5 veined per side; upper surface, 137B, strongly rugose with impressed veins when young, sparsely pale brown 165D stellate pubescent, glabrescent and plus or minus glossy at maturity; undersurface 147C, more densely reddish-brown 166B stellate-pubescent even at maturity, veins raised beneath. Leaves persistent very late into fall, eventually developing fall color and turning deep red, 46B, with strong purple, 79A, yellow, 10B, and orange, 28A, overtones; fall color appears in late October, peaks in early to mid-November and remains effective until late November and occasionally early December.

Flowers: Inforescences terminal, cymose, broadly rounded, 4.5–5 cm in diameter, 2.5–3 cm in length, many flowered (average 67), short pedunculate, the peduncle stellate pubescent; pedicels with a small, stellate-pubescent, papery bract 3–5 mm in length, 1.5 mm in diameter, 165A. Flowers 5-merous, regular, perfect, 9–10 mm in diameter, corolla tube 5.5–7.5 mm long, more or less cylindrical to slightly flared at apex; corolla lobes petaloid, petal lobes ovate, 3.0–4.5 mm in width, 4–6 mm in length, rounded to cuneate, apex rounded, margin erose, minutely papillose; sepals 5 in number, 0.8–1.4 mm in length, 0.6–0.9 mm in width, apex obtuse to rounded, margin translucent and entire, 145B; stamens 5, attached near base of corolla tube; anthers 1.6–2.0 mm in length, 10A; pollen slight, 10D; pistil one in number, 0.7–1.0 mm in length, stigma capitate, with 5 rounded poorly defined lobes, 145A, style 0.5–0.8 mm in length, 46A; corolla reddish in bud, 49D, becoming effective in late April, pure white, 155D, when open, in full bloom in mid-May, persisting 10 to 14 days, flowers strongly aromatic with pleasant clove-like spicy fragrance.

Fruit: Drupe, oblong-ellipsoid, slightly beaked, ca. 10–13 mm long, 7–9 mm wide, 3 mm thick, light green, 144C, in mid-July, red-orange, 46A, in mid-September, black, 202A, by late October at maturity; not ornamental, drops at leaf fall in December; stone 8–9 mm long, ca 6 mm wide, ellipsoid, strongly flattened, shallowly ridged on both faces, light tan, 165C; ultimate pedicels finely stellate-pubescent.

It is claimed:

1. A new and distinct *viburnum* plant originating as a sport of *Viburnum×burkwoodii* 'Sarcoxie' as herein illustrated and described, a shrub characterized by abundant fragrant flowers, glossy foliage, late fall color and compact habit.

* * * * *